United States Patent
Smith et al.

(10) Patent No.: US 10,365,258 B2
(45) Date of Patent: Jul. 30, 2019

(54) METHODS FOR DETERMINING OXIDATION PERFORMANCE OF OXIDATION CATALYST DEVICES

(71) Applicant: GM GLOBAL TECHNOLOGY OPERATIONS LLC, Detroit, MI (US)

(72) Inventors: Michael A. Smith, Clarkston, MI (US); Christopher L. Whitt, Howell, MI (US); Yong Miao, Ann Arbor, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 120 days.

(21) Appl. No.: 15/675,019

(22) Filed: Aug. 11, 2017

(65) Prior Publication Data

US 2019/0049418 A1    Feb. 14, 2019

(51) Int. Cl.
*G01N 33/00*     (2006.01)
*F01N 11/00*     (2006.01)
*F01N 3/10*      (2006.01)

(52) U.S. Cl.
CPC ......... *G01N 33/0037* (2013.01); *F01N 3/103* (2013.01); *F01N 11/007* (2013.01); *F01N 2550/02* (2013.01); *F01N 2560/023* (2013.01); *F01N 2560/026* (2013.01); *F01N 2900/1602* (2013.01); *F01N 2900/1618* (2013.01)

(58) Field of Classification Search
CPC .......... G01N 33/0037; F01N 2560/026; F01N 2550/02; F01N 11/007; Y10T 436/17; Y10T 436/177692; Y10T 436/179228; Y10T 436/208339; Y10T 436/21; Y10T 436/218

USPC ......... 436/37, 106, 116, 118, 137, 139, 143, 436/159

See application file for complete search history.

(56) References Cited

U.S. PATENT DOCUMENTS

| | | | | |
|---|---|---|---|---|
| 7,611,613 B2 * | 11/2009 | Dutta | ................. | G01N 27/4074 204/426 |
| 8,607,546 B2 * | 12/2013 | Sun | ..................... | F02D 41/0235 60/274 |
| 8,776,495 B2 * | 7/2014 | Gonze | ..................... | F01N 3/035 60/284 |

(Continued)

OTHER PUBLICATIONS

Plat et al. Ind. Eng. Chem. Res., vol. 49, 2010, pp. 10348-10357.*

*Primary Examiner* — Maureen Wallenhorst

(57) ABSTRACT

A method for determining the hydrocarbon (HC) oxidation performance of an oxidation catalyst device (OC) includes communicating gas to the OC inlet over a time frame, measuring the NOx content of the OC outlet gas using a NOx sensor over the time frame, wherein the temperature of the OC increases over the time frame, and correlating an increased NOx measurement over the time frame to an increased OC HC oxidation performance. The NOx sensor can be operated in a low temperature mode during the time frame. The method can further include determining the temperature of the OC over the time frame and correlating the HC oxidation performance to the OC temperature, and/or correlating a maximum NOx concentration measured during the time frame to the OC temperature measured at the same time. HC slip through the OC can be identified when the measured NOx content of the OC outlet gas decreases.

16 Claims, 2 Drawing Sheets

(56) References Cited

U.S. PATENT DOCUMENTS

| | | | |
|---|---|---|---|
| 2013/0180231 A1* | 7/2013 | Miao | F01N 3/035 60/297 |
| 2014/0060012 A1* | 3/2014 | Kakimoto | F01N 11/00 60/277 |
| 2014/0144220 A1* | 5/2014 | Ardanese | F01N 11/007 73/114.75 |
| 2018/0038260 A1* | 2/2018 | Miao | F01N 11/007 |
| 2018/0306088 A1* | 10/2018 | Smith | F01N 11/002 |

* cited by examiner

METHODS FOR DETERMINING OXIDATION PERFORMANCE OF OXIDATION CATALYST DEVICES

INTRODUCTION

During a combustion cycle of an internal combustion engine (ICE), air/fuel mixtures are provided to cylinders of the ICE. The air/fuel mixtures are compressed and/or ignited and combusted to provide output torque. After combustion, pistons of the ICE force exhaust gases in the cylinders out through exhaust valve openings and into an exhaust system. The exhaust gas emitted from an ICE, particularly a diesel engine, is a heterogeneous mixture that contains gaseous emissions such as carbon monoxide (CO), unburned hydrocarbons and oxides of nitrogen (NOx), and oxides of sulfur (SOx), as well as condensed phase materials (liquids and solids) that constitute particulate matter. For example, $NO_2$ typically comprises 20% of total $NO_x$ in diesel exhaust. Exhaust gas treatment systems are often employed to reduce $NO_x$ emissions from exhaust gas streams.

Exhaust gas treatment systems may employ catalysts in one or more components configured for accomplishing an after-treatment process. One type of exhaust treatment technology is an oxidation catalyst device (OC), which serves several catalytic functions, including oxidizing NOx, HC, and/or CO species. Further, OCs can convert NO into $NO_2$ to alter the NO:NOx ratio of exhaust gas in order to increase the NOx reduction efficiency of a downstream selective catalytic reduction device. Monitoring performance of OCs remains a challenge.

SUMMARY

A method for determining the hydrocarbon (HC) oxidation performance of an oxidation catalyst device (OC) having an inlet and an outlet is provided. The method includes communicating gas to the OC inlet over a time frame, wherein the exhaust gas comprises NOx and HC species, measuring the NOx content of the OC outlet gas using a NOx sensor over the time frame, wherein the temperature of the OC increases over the time frame, and correlating an increased NOx measurement over the time frame to an increased OC HC oxidation performance. The method can further include determining the temperature of the OC over the time frame and correlating the HC oxidation performance to the OC temperature. The method can further include determining the temperature of the OC over the time frame and identifying an OC HC oxidation light-off temperature by correlating a maximum NOx concentration measured during the time frame to the OC temperature measured at the same time. The NOx content and HC content of the gas can be substantially constant over the time frame. The method can further include operating the NOx sensor in a low temperature mode during the time frame. The method can further include operating NOx sensor in low temperature mode during the time frame, wherein the low temperature is a temperature at which the $NO:NO_2$ equilibrium is kinetically driven. The method can further include operating NOx sensor in low temperature mode below about 300° C. during the time frame. OC HC oxidation performance can be a percent HC oxidation yield. The gas can be generated by an internal combustion engine that powers a vehicle. The time frame can occur proximate a vehicle cold start. The NOx sensor can be an amperometric sensor. The NOx sensor can include a first stage in which the gas contacts a platinum group metal-impregnated zeolite catalyst.

A method for detecting HC slip through an OC is provided. The method includes communicating gas to the OC inlet over a time frame, wherein the exhaust gas comprises NOx and HC species, measuring the NOx content of the OC outlet gas of the OC using a NOx sensor over the time frame, and identifying HC slip through the OC when the measured NOx content of the OC outlet gas decreases. The NOx content and HC content of the gas can be substantially constant over the time frame. The method can further include operating the NOx sensor in a low temperature mode during the time frame. The method can further include operating NOx sensor in low temperature mode during the time frame, wherein the low temperature is a temperature at which the $NO:NO_2$ equilibrium is kinetically driven. The method can further include operating NOx sensor in low temperature mode below about 300° C. during the time frame. The gas can be generated by an internal combustion engine that powers a vehicle. The NOx sensor can be an amperometric sensor. The NOx sensor can include a first stage a platinum group metal-impregnated zeolite catalyst.

Other objects, advantages and novel features of the exemplary embodiments will become more apparent from the following detailed description of exemplary embodiments and the accompanying drawings.

DETAILED DESCRIPTION

Figure 1:
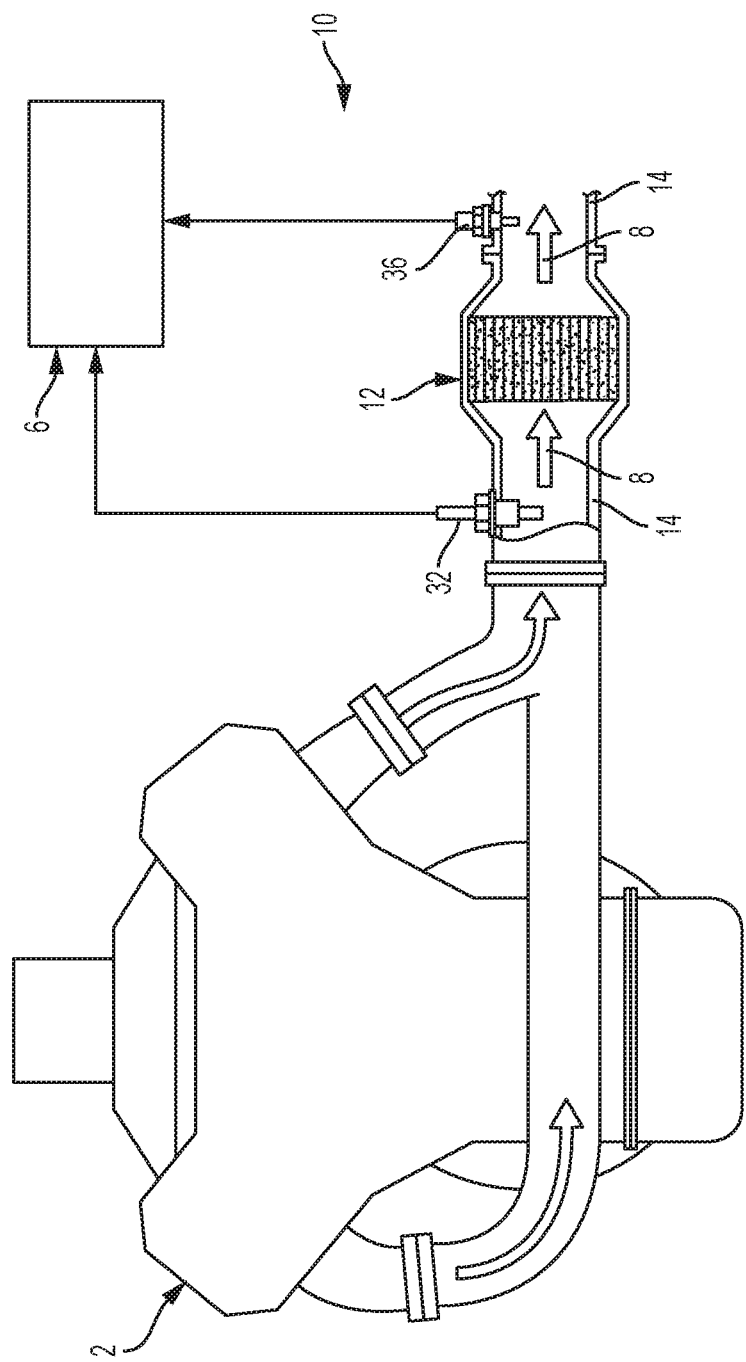
FIG. 1 illustrates an exhaust gas treatment system, according to one or more embodiments.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Generally, this disclosure pertains to gas sensors and methods of determining the concentration of oxides of nitrogen ($NO_x$) in a gaseous sample. In particular, this disclosure pertains to NOx sensors used to determine NO and NO2 concentrations in exhaust gas streams. Exhaust gas streams are generated, in some embodiments, by internal combustion engines (ICE) which can, for example, power a vehicle. As used herein, "$NO_x$" refers to one or more nitrogen oxides. $NO_x$ species can include $N_yO_x$ species, wherein y>0 and x>0. Non-limiting examples of nitrogen oxides can include NO, $NO_2$, $N_2O$, $N_2O_2$, $N_2O_3$, $N_2O_4$, and $N_2O_5$.

Many of the NOx sensors rely on the potentiometric (i.e., mixed potential) or amperometric measurement of oxygen partial pressure resulting from the decomposition of $NO_2$ molecules to NO, and NO to $N_2$ and $O_2$ in order to determine $NO_x$ concentration. Amperometric $NO_x$ sensors determine total $NO_x$ concentration by reducing $NO_x$ species within a sample and measuring the liberated oxygen species. Because $NO_2$ and NO will liberate different quantities of oxygen, this method of operation imposes an inherent cross-sensitivity to $NO_x$ species (e.g., $NO_2$ and NO). As described here, such cross-sensitivity is advantageously utilized for monitoring and controlling various exhaust gas treatment devices.

$NO_x$ sensors, such as an amperometric $NO_x$ sensor, generally comprise two stages: a first background oxygen purge stage, and a second $NO_x$ species measuring stage. Background oxygen is purged in the first stage so that it does not interfere with accurate measurement of $NO_x$ species in the second stage. A gas sample containing $NO_x$ species is introduced to the first stage, and oxygen species are purged out via one or more methods. The first stage can include a $NO_2$ selective reduction catalyst for reducing $NO_2$ species to NO. Complete reduction of all $NO_2$ to NO is preferred in the first stage in order to prevent $NO_2$ dissociated oxygen species from being double counted in the second stage. Purged background oxygen species in this first stage can include oxygen species germane to the gas sample, and oxygen species generated during the selective reduction of $NO_2$ species. Background oxygen species can be purged, for example, using electrochemical pumps. Electrochemical pumps apply a bias (e.g., −200 mV to −400 mV) which reduces diatomic oxygen to $O^=$ and pumps the ions from the stage. Pumping current can be proportional to the amount of oxygen present in the stage.

The $NO_2$ selective reduction catalyst can comprise any suitable catalyst which reduces $NO_2$ to NO. For example. the selective reduction $NO_x$ catalyst can operate to selectively reduce $NO_2$ to NO. Selectivity can include complete selectivity or partial selectivity. In some embodiments, the $NO_2$ selective reduction catalyst is one which will not reduce NO (i.e., complete selectivity). In some embodiments, suitable materials for $NO_2$ selective reduction catalysts can include rhodium or platinum, for example. In some embodiments, the catalyst can include one or more platinum group metal catalysts. Suitable platinum group metals include Pt, Pd, Rh, Ru, Os or Ir, or combinations thereof including alloys thereof. NOx conversation rates by such catalysts are controlled by reaction kinetics at low temperatures (e.g., <300° C.) and by thermodynamic constraints at higher temperatures (e.g., >300° C.), generally resulting in an equilibrium governed by Equation (1):

$$NO + \tfrac{1}{2}O_2 \leftrightarrow NO_2 \quad (1)$$

In this relationship, the total system $NO_x$ concentration can be simplified as substantially the sum of NO and $NO_2$, in which the concentration of $NO_2$ varies inversely with temperature. For example, at 100° C. the $NO_2$:NO ratio can approach a maximum limit (i.e. 100% $NO_2$), whereas at about 300 to 400° C. the $NO_2$:NO ratio can be approximately 1, and at about 700° C. or above the $NO_2$:NO ratio can be 1:20 or less. Accordingly, NOx sensors are typically operated at high temperatures (e.g., >700° C.) in order to maximize the NO:$NO_2$ ratio. In some embodiments, a $NO_2$ selective reduction catalyst comprises a heating element, which increases the temperature of a gas sample such that the $NO_2$:NO ratio is decreased. The heating element can be in the form of a heating electrode formed about the stage or the entire $NO_x$ sensor, for example. The operating temperature of a sensor can be the temperature of the catalyst.

In the second stage of the $NO_x$ sensor, $NO_x$ species (i.e., NO) are catalytically decomposed to $N_2$ and $O_2$. The second stage generally detects the partial pressure of oxygen whose volume is increased as a function of the amount of the $NO_x$ catalytically reduced. Catalytic decomposition can be effected utilizing a reduction catalyst comprising rhodium or platinum, for example. In some embodiments, the catalyst can include one or more platinum group metal catalysts. Suitable platinum group metals include Pt, Pd, Rh, Ru, Os or Ir, or combinations thereof, including alloys thereof. The reduction catalyst can include a catalytic electrode. The dissociated oxygen is then pumped from the stage and measured. Dissociated oxygen can be measured volumetrically, as a change in voltage within an oxygen concentration cell, or based upon the pumping current, for example.

$NO_x$ sensors are commonly utilized in exhaust gas treatment systems. FIG. 1 illustrates an exhaust gas treatment system 10 for treating and/or monitoring the exhaust gas 8 constituents of an ICE 2. The exhaust gas treatment system 10 described herein can be implemented in various ICE 10 systems that can include, but are not limited to, diesel engine systems, gasoline direct injection systems, and homogeneous charge compression ignition engine systems. The ICEs will be described herein for use in generating torque for vehicles, yet other non-vehicular applications are within the scope of this disclosure. Therefore when reference is made to a vehicle, such disclosure should be interpreted as applicable to any application of an ICE. Moreover, ICE 2 can generally represent any device capable of generating an exhaust gas 8 comprising $NO_x$ species, and the disclosure herein should accordingly be interpreted as applicable to all such devices. It should be further understood that the embodiments disclosed herein may be applicable to treatment of effluent streams not comprising $NO_x$ species, and, in such instances, ICE 2 can also generally represent any device capable of generating an effluent stream comprising not comprising $NO_x$ species. For Example, ICE 2 can include a plurality of reciprocating pistons (not shown) attached to a crankshaft (not shown), which may be operably attached to a driveline, such as a vehicle driveline (not shown), to deliver tractive torque to the driveline. For example, ICE 2 can be any engine configuration or application, including various vehicular applications (e.g., automotive, marine and the like), as well as various non-vehicular applications (e.g., pumps, generators and the like).

The exhaust gas treatment system 10 generally includes one or more exhaust gas conduits 14, and one or more exhaust treatment devices, such as oxidation catalyst (OC) device 12 in fluid communication with ICE 2. The exhaust gas conduit 14, which can comprise several segments, transports exhaust gas 8 from the ICE 2 to the various exhaust treatment devices of the exhaust gas treatment system 10. In some exemplary embodiments, exhaust gas 8 can comprise $NO_x$ species.

The exhaust gas treatment system 10 further generally includes downstream $NO_x$ sensor 36 and optionally upstream $NO_x$ sensor 32. As used herein, a component being located upstream relative to a downstream component generally means that it is relatively closer to the ICE 2, or that exhaust gas 8 arrives at the upstream component prior to the downstream component. Downstream $NO_x$ sensor 36 and optional upstream $NO_x$ sensor 32 can be operatively connected to electronic engine control module (ECM) 6 that may be configured to accomplish control within exhaust gas 8 in accordance with control methods and strategies described herein. As used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality. The exhaust gas treatment system 10 can optionally further include one or more additional exhaust treatment devices (not shown), including a particulate filter device, a selective catalytic reduction (SCR) device, and a selective catalytic reduction filter (SCRF) device. For example, in some embodiments, the OC device 12, such as a diesel oxidation catalyst device, can be positioned upstream of an SCR device or SCRF device to convert NO into $NO_2$ for preferential treatment in the SCR device or SCRF device.

OC 12 is a flow-through device comprising a catalytic composition (CC) and configured to accept exhaust gas 8. OC 12 is generally utilized to oxidize various exhaust gas 8 species, including HC species, CO, and $NO_x$ species. CC can be housed within a housing, such as a metal housing, having an inlet (i.e., upstream) opening and outlet (i.e., downstream) opening, or be otherwise configured to provide structural support and facilitate fluid (e.g., exhaust gas) flow through OC 12. The housing can ideally comprise a substantially inert material, relative to the exhaust gas constituents, such as stainless steel, and may comprise any suitable shape or size including a cylindrically shaped compartment. The compartment further may include attachment features, such as a cylindrical inlet pipe located proximate an inlet opening and a cylindrical outlet pipe located proximate an outlet opening of the compartment for fluid coupling of OC 12 to exhaust gas conduit 9 and/or another component of the exhaust gas treatment system 10.

CC can comprise many various first oxidation catalyst materials, and physical configurations thereof, for oxidizing HC, CO, and NOx. CC can further comprise a substrate such as a porous ceramic matrix or the like, for example. Substrates can comprise alumina, silica, zeolite, zirconia, titania, and/or lanthana, for example. First oxidation catalyst materials can comprise platinum group metal catalysts, metal oxide catalysts, and combinations thereof. Suitable platinum group metal catalysts can include platinum (Pt), palladium (Pd), rhodium (Rh), ruthenium (Ru), osmium (Os), or iridium (Ir), and combinations thereof, including alloys thereof. In one embodiment, suitable metals include Pt, Pd, Rh, and combinations thereof, including alloys thereof. Suitable metal oxide catalysts can include iron oxides, zinc oxides, aluminum oxides, perovskites, and combination thereof, for example. In one embodiment, CC can comprise Pt and $Al_2O_3$. It is to be understood that the CC is not limited to the particular examples provided, and can include any catalytically active device capable of oxidizing HC species, CO, and NOx species. In many embodiments, CC comprises zeolite impregnated with one or more catalytically active base metal components. The zeolite can comprise a (β-type zeolite, a Y-type zeolite, a ZM5 zeolite, or any other crystalline zeolite structure such as a Chabazite or a USY (ultra-stable Y-type) zeolite. In a particular embodiment, the zeolite comprises Chabazite. In a particular embodiment, the zeolite comprises SSZ, wherein SSZ comprises a high silica zeolite with a Si:Al ratio greater than about 5. The OC 12 CCs disclosed herein are similarly suitable for use in the first stage of the NOx sensors described above.

OC 12 can store and/or oxidize NOx species in exhaust gas 8, which, for example, may form during the combustion of fuel. For example, in some embodiments, OC 12 can be utilized to convert NO into $NO_2$ in order to optimize the exhaust gas $NO:NO_2$ ratio for downstream SCRs and/or SCRFs which generally operate more efficiently with exhaust gas feed streams having a $NO:NO_2$ ratio of about 1:1. For example, exhaust 8 emitted from OC 12 can be about 40% to about 60% $NO_2$. Accordingly, OC 12 is disposed upstream from SCR 20.

OC 12 are additionally or alternatively utilized to catalyze the oxidation (e.g., combustion) of HC, $H_2$, and CO species in exhaust gas. Combustion generally involves the oxidation of HC and/or CO species in the presence of oxygen to generate heat, water, and $CO_2$. In some instances, HC, $H_2$, and/or CO may be present in exhaust gas 8 as a consequence of undesired incomplete combustion of fuel, for example. In other instances, HC may be present in exhaust gas 8 in order to implement various ICE 2 and/or system 10 control strategies. For example, exothermic oxidation of HC can OC 12 can be utilized to oxidize HC to provide heat to system 10 to aid one or more exhaust gas treatment devices achieve light-off temperatures. In nearly all instances, HC, $H_2$, and/or CO slip through OC 12 is undesired. It can be difficult to monitor slip of HC, $H_2$, and/or CO slip through OC 12.

OC 12 can have a light-off temperature above which CC exhibits desired or suitable catalytic activity relating to the oxidation of HC, $H_2$, and/or CO species. The light-off temperature can be dependent upon the type of catalytic materials of which CC is comprised, and the amount of catalytic materials present in OC 12, among other factors. Many aspects of system 10, including calibration and operation of ICE 2, are designed to accommodate the light-off temperature(s) of OC 12. It can be difficult to accurately determine the HC, $H_2$, and/or CO species oxidation light-off temperature(s) of a given OC 12, particularly as OC 12 ages over time, or operates under varying conditions, for example.

Provided herein are methods for determining OC 12 light-off temperatures and for monitoring HC, $H_2$, and/or CO species slip through OC 12. The methods utilize a phenomenon in which HC reduces $NO_2$ to NO in the presence of oxidizing catalysts such as the catalysts utilized in a NOx sensor first stage as described above. The phenomenon occurs even at low temperatures (e.g., <300° C.) where the reaction kinetics-driven equilibrium strongly favors $NO_2$ over NO. Because the methods below are commonly implemented using low NOx sensor operating temperatures, the methods are particular advantageous during vehicle cold starts during which NOx sensor heating is typically delayed to prevent moisture from cracking of ceramic components. The methods will be described with reference to system 10 illustrated in FIG. 1 for the purpose of clarity only, and said methods are not intended to be limited thereto.

Figure 2:
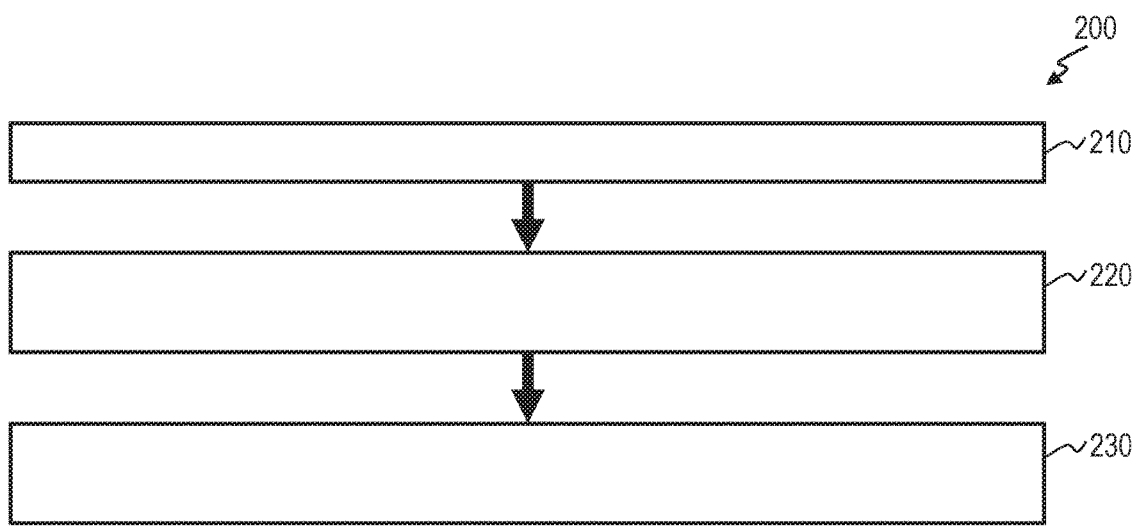
FIG. 2 illustrates a method for determining an the hydrocarbon oxidation performance of an oxidation catalyst device, according to one or more embodiments.

FIG. 2 illustrates a method 200 for determining an OC 12 HC oxidation performance, wherein the method comprises communicating 210 exhaust gas 8 to the OC 12 inlet for a time frame, measuring 220 the outlet exhaust gas 8 of OC 12 using a NOx sensor 36 over the time frame, and correlating 230 an increased NOx measurement over the time frame to an increased OC 12 HC oxidation performance. The NOx sensor 36 utilizes an oxidizing catalyst in a first stage, and can comprise an amperometric sensor. The temperature of OC 12 generally increases over the time frame. The temperature increase of OC 12 can be effected by heat imparted by exhaust gas 8, or by other means such as an electrically heated catalyst (not shown). OC 12 HC oxidation performance can comprise a percent HC oxidation yield, for example.

Temporally proximate the beginning of the time frame, $NO_2$ in exhaust gas 8 emitted from OC 12 will be reduced by HC in the NOx sensor 36 first stage at a particular rate. Later in the time frame, as OC 12 begins to increase in temperature, a higher amount of HC is oxidized in OC 12 and less $NO_2$ is reduced in the NOx sensor 36 first stage. Accordingly, more $NO_2$ enters the NOx sensor 36 second stage and a higher amount of dissociated oxygen (i.e., a higher NOx concentration) is measured. In some embodiments, in order to utilize a higher, more statistically significant amount of $NO_2$ within the NOx sensor 36 first stage, the NOx sensor 36 can operate in a low temperature mode during the time frame. For example, NOx sensor 36 can operate at a temperature of less than about 300° C. In some embodiments, the NOx sensor 36 can operate in a low temperature mode during the time frame such that the temperature at which the $NO:NO_2$ equilibrium is kinetically driven. In some embodiments the NOx content and/or HC content of the exhaust gas 8 is substantially constant over the time frame. In other embodiments, the NOx content and/or HC content of the exhaust gas 8 varies over the time frame. In such embodiments, the variance(s) can be accounted for in correlating increasing NOx concentration to increased OC 12 HC oxidation performance. The exhaust gas 8 can be generated by an ICE (e.g., ICE 2) which powers a vehicle (not shown). In such an embodiment, the time frame can occur proximate a vehicle cold start.

Method 200 can further comprise determining the temperature of OC 12 during the time frame, and correlating the OC 12 HC oxidation performance to OC 12 temperature. Determining OC temperature can comprise measuring using a temperature sensor (not shown), or computing using a model, among other means. In some embodiments, method 200 can further comprise determining the temperature of OC 12 during the time frame, and identifying an OC 12 HC oxidation light-off temperature by correlating a maximum NOx concentration measured during the time frame to the OC 12 temperature measured at the same time. When the measured NOx concentration achieves a maximum or enters a horizontal asymptote (i.e., a plateau), it is presumed that all HC within exhaust gas 8 has been oxidized within OC 12. In such an instance, the OC 12 HC oxidation light-off temperature identifies a temperature at which the OC 12 oxidizes all, or substantially all HC within exhaust gas 8. The OC 12 HC oxidation performance and/or OC 12 HC oxidation light-off temperature can further be utilized to determine OC 12 $H_2$ and/or CO oxidation performance, for example by using the Arhenius equation.

Figure 3:
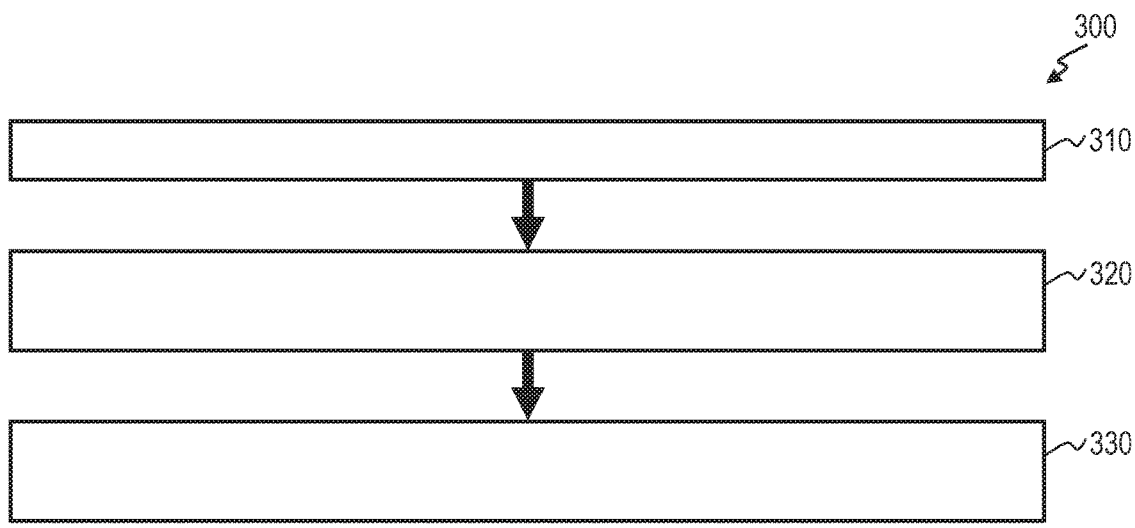
FIG. 3 illustrates a method for using an amperometric gas sensor, according to one or more embodiments.

FIG. 3 illustrates a method 300 for detecting HC slip during operation of OC 12 having an inlet and an outlet, comprising communicating 310 exhaust gas 8 to the OC 12 inlet over a time frame, wherein the exhaust gas comprises NOx and HC species, measuring 320 the NOx content of the OC 12 outlet gas of the OC 12 using a NOx sensor 36 over the time frame; and identifying 330 HC slip through OC 12 when the measured NOx content of the OC 12 outlet exhaust gas 8 decreases. The NOx sensor 36 utilizes an oxidizing catalyst in a first stage, and can comprise an amperometric sensor. In some embodiments the NOx sensor 36 can operate in a low temperature mode during the time frame. For example, NOx sensor 36 can operate at a temperature of less than about 300° C. In some embodiments, the NOx sensor 36 can operate in a low temperature mode during the time frame such that the temperature at which the $NO:NO_2$ equilibrium is kinetically driven. In some embodiments the NOx content and/or HC content of the exhaust gas 8 is substantially constant over the time frame. In other embodiments, the NOx content and/or HC content of the exhaust gas 8 varies over the time frame. In such embodiments, the variance(s) can be accounted for in correlating increasing NOx concentration to increased OC 12 HC oxidation performance. The exhaust gas 8 can be generated by an ICE (e.g., ICE 2) which powers a vehicle (not shown). In such an embodiment, the time frame can occur proximate a vehicle cold start, or during normal vehicle operation.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

What is claimed is:

1. A method for determining a hydrocarbon (HC) oxidation performance of an oxidation catalyst device (OC) having an inlet and an outlet, the method comprising:
   communicating exhaust gas to the OC inlet over a time frame, wherein the exhaust gas comprises NOx and HC species;
   measuring a NOx content of an OC outlet gas using a NOx sensor over the time frame, wherein a temperature of the OC increases over the time frame; and
   correlating an increased NOx measurement over the time frame to an increased OC HC oxidation performance, wherein the NOx sensor is operated in a low temperature mode during the time frame characterized by an operating temperature at which a $NO:NO_2$ equilibrium is kinetically driven.

2. The method of claim 1, further comprising determining a temperature of the OC over the time frame and correlating the HC oxidation performance to the OC temperature using a light-off temperature specific to one or more chemical species.

3. The method of claim 1, further comprising determining a temperature of the OC over the time frame and identifying an OC HC oxidation light-off temperature by correlating a maximum NOx concentration measured during the time frame to the OC temperature measured at the same time.

4. The method of claim 1, wherein a NOx content and a HC content of the exhaust gas communicated to the OC inlet is substantially constant over the time frame.

5. The method of claim 1, wherein the operating temperature is below about 300° C. during the time frame.

6. The method of claim 1, wherein OC HC oxidation performance comprises a percent HC oxidation yield.

7. The method of claim 1, wherein the exhaust gas is generated by an internal combustion engine that powers a vehicle.

8. The method of claim 7, wherein the time frame occurs proximate a vehicle cold start.

9. The method of claim 1, wherein the NOx sensor comprises an amperometric sensor.

10. The method of claim 1, wherein the NOx sensor comprises a first stage in which the exhaust gas contacts a platinum group metal-impregnated zeolite catalyst.

11. A method for detecting hydrocarbon (HC) slip through an oxidation catalyst device (OC) having an inlet and an outlet, the method comprising:
communicating exhaust gas to the OC inlet over a time frame, wherein the exhaust gas comprises NOx and HC species;
measuring a NOx content of an OC outlet gas of the OC using a NOx sensor over the time frame; and
identifying HC slip through the OC when the measured NOx content of the OC outlet gas decreases,
wherein the NOx sensor is operated in a low temperature mode during the time frame characterized by an operating temperature at which a NO:$NO_2$ equilibrium is kinetically driven.

12. The method of claim 11, wherein a NOx content and a HC content of the exhaust gas communicated to the OC inlet is substantially constant over the time frame.

13. The method of claim 11, wherein the operating temperature is below about 300° C. during the time frame.

14. The method of claim 11, wherein the exhaust gas is generated by an internal combustion engine that powers a vehicle.

15. The method of claim 11, wherein the NOx sensor comprises an amperometric sensor.

16. The method of claim 11, wherein the NOx sensor comprises a first stage in which the exhaust gas contacts a platinum group metal-impregnated zeolite catalyst.

* * * * *